US006392102B1

(12) United States Patent
Hagen et al.

(10) Patent No.: US 6,392,102 B1
(45) Date of Patent: May 21, 2002

(54) PREPARATION OF POLYOXYMETHYLENE DIMETHYL ETHERS BY CATALYTIC CONVERSION OF FORMALDEHYDE FORMED BY OXIDATION OF DIMETHYL ETHER

(75) Inventors: Gary P. Hagen, West Chicago; Michael J. Spangler, Sandwich, both of IL (US)

(73) Assignee: BP Corporation North America Inc., Chicago, IL (US)

( * ) Notice: Subject to any disclaimer, the term of this patent is extended or adjusted under 35 U.S.C. 154(b) by 0 days.

(21) Appl. No.: 09/547,515

(22) Filed: Apr. 12, 2000

Related U.S. Application Data

(63) Continuation-in-part of application No. 09/191,405, filed on Nov. 12, 1998, now abandoned, which is a continuation-in-part of application No. 09/190,315, filed on Nov. 12, 1998, now abandoned.

(51) Int. Cl.$^7$ ......................... C07C 47/00; C07C 45/00; C07C 43/11; C07C 43/18
(52) U.S. Cl. ..................... 568/420; 568/410; 568/618; 568/613; 568/621
(58) Field of Search ................................. 560/420, 470, 560/618, 613, 621

(56) References Cited

U.S. PATENT DOCUMENTS 3,655,771 A * 4/1972 Tadnuma et al. ........... 260/603

FOREIGN PATENT DOCUMENTS

CH         688041 A5 * 6/1994

* cited by examiner

Primary Examiner—Johann Richter
Assistant Examiner—Diedra Faulkner
(74) Attorney, Agent, or Firm—Ekkehard Schoettle

(57) ABSTRACT

A particularly useful process which includes the steps of providing a feedstream comprising providing a source of formaldehyde formed by conversion of dimethyl ether in the presence of a catalyst comprising tungsten oxide; and (i) heating the feedstream with the heterogeneous acidic catalyst in a catalytic distillation column to convert methanol and formaldehyde present to methylal and higher polyoxymethylene dimethyl ethers and to separate the methylal from the higher polyoxymethylene dimethyl ethers is disclosed, and/or (ii) contacting the source of formaldehyde and a predominately dimethyl ether feedstream with a heterogeneous, condensation promoting catalyst capable of hydrating dimethyl ether under conditions of reaction sufficient to form an effluent comprising water, methanol, formaldehyde, dimethyl ether, and polyoxymethylene dimethyl ethers is disclosed. Unreacted dimethyl ether is recovered from the effluent and recycled to the formation of polyoxymethylene dimethyl ethers. The resulting dimethyl ether-free liquid mixture is heated in the presence of an acidic catalyst to convert at least the methanol and formaldehyde present to polyoxymethylene dimethyl ethers. Advantageously, methylal and higher polyoxymethylene dimethyl ethers are formed and separated in a catalytic distillation column. By including in the column an anion exchange resin, an essentially acid-free product is obtained which can be used directly as a blending component, or fractionated, as by further distillation, to provide more suitable components for blending into diesel fuel.

20 Claims, 2 Drawing Sheets

PREPARATION OF POLYOXYMETHYLENE DIMETHYL ETHERS BY CATALYTIC CONVERSION OF FORMALDEHYDE FORMED BY OXIDATION OF DIMETHYL ETHER

CROSS-REFERENCE TO RELATED APPLICATION

This application is a CIP of U.S. application Ser. No. 09/191,405 filed Nov. 12, 1998, now abandoned which is a CIP of U.S. application Ser. No. 09/190,315 filed Nov. 12, 1998, now abandoned which applications are specifically incorporated herein, in their entirety, by reference.

TECHNICAL FIELD

The present invention relates to production of organic compounds, particularly polyoxymethylene dimethyl ethers, which are suitable components for blending into fuel having improved qualities for use in diesel engines. More specifically, it relates to (i) to providing a feedstream comprising methanol, formaldehyde and a soluble condensation promoting component capable of activating a heterogeneous acidic catalyst, and heating this feedstream with the heterogeneous acidic catalyst in a catalytic distillation column to convert methanol and formaldehyde present to methylal and higher polyoxymethylene dimethyl ethers and separate the methylal from the higher polyoxymethylene dimethyl ethers, and/or alternatively (ii) to employing a heterogeneous, condensation promoting catalyst capable of hydrating dimethyl ether in conversion of dimethyl ether and formaldehyde to form a condensation effluent. A dimethyl ether-free mixture, separated form the effluent, is heated in a catalytic distillation column to convert methanol and formaldehyde present to methylal and higher polyoxymethylene dimethyl ethers and separate the methylal from the higher polyoxymethylene dimethyl ethers. Advantageously, the catalytic distillation column has a section containing an anion exchange resin whereby an essentially acid-free product is obtained which can be used directly as a blending component, or fractionated, as by further distillation, to provide more suitable components for blending into diesel fuel.

This integrated process also provides its own source of formaldehyde which is an un-purified liquid stream derived from a mixture formed by oxidation of dimethyl ether with a catalytically effective amount of an oxidation promoting catalyst comprising tungsten oxide as an essential catalyst component.

BACKGROUND OF THE INVENTION

Conversion of low molecular weight alkanes such as methane to synthetic fuels or chemicals has received increasing attention because low molecular weight alkanes are generally available from secure and reliable sources. For example, natural gas wells and oil wells currently produce vast quantities of methane. Reported methods for converting low molecular weight alkanes to more easily transportable liquid fuels and chemical feedstocks can be conveniently categorized as direct oxidative routes and/or as indirect syngas routes. Direct oxidative routes convert lower alkanes to products such as methanol, gasoline, and relatively higher molecular weight alkanes. In contrast, indirect syngas routes typically involve production of synthesis gas as an intermediate product.

Routes are known for converting methane to dimethyl ether. For example, methane is steam reformed to produce synthesis gas. Thereafter, dimethyl ether and methanol can be manufactured simultaneously from the synthesis gas, as described in U.S. Pat. No. 4,341,069 issued to Bell et al. They recommend a dimethyl ether synthesis catalyst having copper, zinc, and chromium co-precipitated on a gamma-alumina base. Alternatively, methane is converted to methanol, and dimethyl ether is subsequently manufactured from methanol by passing a mixed vapor containing methanol and water over an alumina catalyst, as described in an article by Hutchings in New Scientist (Jul. 3, 1986) 35.

Formaldehyde is a very important intermediate compound in the chemical industry. The extreme reactivity of the formaldehyde carbonyl group and the nature of the molecule as a basic building block has made formaldehyde an important feedstock for a wide variety of industrially important chemical compounds. Historically, formaldehyde has found its largest volume of application in the manufacture of phenol-formaldehyde resins, urea-formaldehyde resins and other polymers. Pure formaldehyde is quite uncommon since it polymerizes readily. It was usually obtained as an aqueous solution such as formalin, which contains only about 40 percent formaldehyde. However, more recently, formaldehyde is usually transported as an item of commerce in concentrations of 37 to 50 percent by weight. A solid source of formaldehyde called paraformaldehyde is also commercially available.

Because of the reactivity of formaldehyde, its handling and separation require special attention. It is a gas above −19° C. and is flammable or explosive in air at concentrations of about 7 to about 12 mol percent. Formaldehyde polymerizes with itself at temperatures below 100° C. and more rapidly when water vapor or impurities are present. Since formaldehyde is usually transported in aqueous solutions of 50 percent by weight or lower concentration, producers have tended to locate close to markets and to ship the methanol raw material, which has a smaller volume.

It is known that some reactions may be carried out by means of catalytic distillation. In catalytic distillation, reaction and separation are carried out simultaneously in a distillation column with internal and/or external stages of contact with catalyst.

In U.S. Pat. No. 4,215,011, Smith, Jr. discloses a method for the separation of an isoolefin, preferably having four to six carbon atoms, from streams containing mixtures thereof with the corresponding normal olefin, wherein the mixture is fed into a reaction-distillation column containing a fixed-bed, acidic cation exchange resin and contacted with the acidic cation exchange resin to react the isoolefin with itself to form a dimer and the dimer is separated from the normal olefin, the particulate catalytic material, i.e., the acidic cation exchange resin, being contained in a plurality of closed cloth pockets, which pockets are arranged and supported in the column by wire mesh.

In U.S. Pat. No. 4,443,559, Smith, Jr. discloses a catalytic distillation structure which comprises a catalyst component associated intimately with or surrounded by a resilient component, which component is comprised of at least 70 vol. percent open space for providing a matrix of substantially open space. Examples of such resilient component are open-mesh, knitted, stainless wire (demister wire or an expanded aluminum); open-mesh, knitted, polymeric filaments of nylon, Teflon, etc.; and highly-open structure foamed material (reticulated polyurethane).

In U.S. Pat. No. 5,113,015, David A. Palmer, K. D. Hansen and K. A. Fjare disclose to a process for recovering acetic acid from methyl acetate wherein the methyl acetate is hydrolyzed to methanol and acetic acid via catalytic distillation.

In German Democratic Republic DD 245 868 A1 published May 20, 1987 in the text submitted by the applicant, preparation of methylal is carried out by reaction of methanol with trioxane, formalin or paraformaldehyde in the presence of a specific zeolite. Autoclave reactions of 1 to 8 hours are described using a zeolite of the "LZ40 type" with a ratio of silicon dioxide to alumina ratio of 78 at temperatures from 493 to 543 K. Methylal content of the product as high as 99.8 percent (without methanol) is reported for trioxane at 523 K for 3 hours. Reaction pressures did not exceed 5 MPa in the autoclave. Neither conversions nor selectivity are reported.

In U.S. Pat. No. 4,967,014, Junzo Masamoto, Junzo Ohtake and Mamoru Kawamura describe a process for formaldehyde production by reacting methanol with formaldehyde to form methylal, $CH_3OCH_2OCH_3$, and then oxidizing the resulting methylal to obtain formaldehyde. In the methylal formation step, a solution containing methanol, formaldehyde and water was brought into solid-liquid contact with a solid acid catalyst, and a methylal-rich component was recovered as a distillate. This process employs reactive distillation performed using a distillation column and multireaction units. The middle portion of the distillation column was furnished with stages from which the liquid components were withdrawn and pumped to the reactor units, which contained solid acid catalyst. The reactive solutions containing the resulting methylal were fed to the distillation column, where methylal was distilled as the overhead product.

Polyoxymethylene dimethyl ethers are the best known members of the dialkyl ether polymers of formaldehyde. While diethyl and dipropyl polyoxymethylene ethers have been prepared, major attention has been given to the dimethyl ether polymers. Polyoxymethylene dimethyl ethers make up a homologous series of polyoxymethylene glycol derivatives having the structure represented by use of the type formula indicated below:

$$CH_3O(CH_2O)_nCH_3$$

Chemically, they are acetals closely related to methylal, $CH_3OCH_2OCH_3$, which may be regarded as the parent member of the group in which n of the type formula equals 1. They are synthesized by the action of methanol on aqueous formaldehyde or polyoxymethylene glycols in the presence of an acidic catalyst just as methylal is produced. On hydrolysis they are converted to formaldehyde and methanol. Like other acetals, they possess a high degree of chemical stability. They are not readily hydrolyzed under neutral or alkaline conditions, but are attacked by even relatively dilute acids. They are more stable than the polyoxymethylene diacetates.

Due to the relatively small differences in the physical properties (melting points, boiling points, and solubility) of adjacent members in this series, individual homologs are not readily separated. However, fractions having various average molecular weight values have been isolated. The normal boiling point temperature of a fraction having average n of 2 in the type formula is reported as 91° to 93° C. Boiling points at atmospheric pressure calculated from partial pressure equations range from 105.0° C. for n of 2, to 242.3° C. for n of 5. (Walker, Joseph Frederic, "Formaldehyde", Robert E. Krieger Publishing Co., issued as No. 159 of American Chemical Society Monograph series (1975), pages 167–169)

Polyoxymethylene dimethyl ethers are prepared in laboratory scale by heating polyoxymethylene glycols or paraformaldehyde with methanol in the presence of a trace of sulfuric or hydrochloric acid in a sealed tube for 15 hours at 150° C., or for a shorter time (12 hours) at 165° to 180° C. Considerable pressure is caused by decomposition reactions, which produce carbon oxides, and by formation of some dimethyl ether. The average molecular weight of the ether products increases with the ratio of paraformaldehyde or polyoxymethylene to methanol in the charge. A high polymer is obtained with a 6 to 1 ratio of formaldehyde (as polymer) to methanol. In these polymers, the n value of the type formula $CH_3O(CH_2O)_nCH_3$ is greater than 100, generally in the range of 300 to 500. The products are purified by washing with sodium sulfite solution, which does not dissolve the true dimethyl ethers, and may then be fractionated by fractional crystallization from various solvents.

U.S. Pat. No. 2,449,469 in the names of W. F. Gresham and R. E. Brooks reported obtaining good yields of polyoxymethylene dimethyl ethers containing 2 to 4 formaldehyde units per molecule. This procedure is carried out by heating methylal with paraformaldehyde or concentrated formaldehyde solutions in the presence of sulfuric acid.

In the past, various molecular sieve compositions, natural and synthetic, have been found to be useful for a number of hydrocarbon conversion reactions. Among these are alkylation, aromatization, dehydrogenation and isomerization. Among the sieves which have been used are Type A, X, Y and those of the MFI crystal structure as shown in "Atlas of Zeolite Structure Types," Second Revised Edition, 1987, published on behalf of the Structure Commission of the International Zeolite Associates and incorporated by reference herein. Representative of the last group are ZSM-5 and AMS borosilicate molecular sieves.

Prior art developments have resulted in the formation of many synthetic crystalline materials. Crystalline aluminosilicates are the most prevalent and, as described in the patent literature and in the published journals, are designated by letters or other convenient symbols. Exemplary of these materials are Zeolite A (Milton, in U.S. Pat. No. 2,882,243), Zeolite X (Milton, in U.S. Pat. No. 2,882,244), Zeolite Y (Breck, in U.S. Pat. No. 3,130,007), Zeolite ZSM-5 (Argauer, et al., in U.S. Pat. No. 3,702,886), Zeolite ZSM-11 (Chu, in U.S. Pat. No. 3,709,979), Zeolite ZSM-12 (Rosinsid, et al., in U.S. Pat. No. 3,832,449), and others.

It is well known that internal combustion engines have revolutionized transportation following their invention during the last decades of the 19th century. While others, including Benz and Gottleib Wilhelm Daimler, invented and developed engines using electric ignition of fuel such as gasoline, Rudolf C. K. Diesel invented and built the engine named for him which employs compression for autoignition of the fuel in order to utilize low-cost organic fuels. Development of improved diesel engines for use in automobiles has proceeded hand-in-hand with improvements in diesel fuel compositions, which today are typically derived from petroleum. Modern high performance diesel engines demand ever more advanced specification of fuel compositions, but cost remains an important consideration.

Even in newer, high performance diesel engines combustion of conventional fuel produces smoke in the exhaust. Oxygenated compounds and compounds containing few or no carbon-to-carbon chemical bonds, such as methanol and dimethyl ether, are known to reduce smoke and engine exhaust emissions. However, most such compounds have high vapor pressure and/or are nearly insoluble in diesel fuel, and they have poor ignition quality, as indicated by their cetane numbers. Furthermore, other methods of improving diesel fuels by chemical hydrogenation to reduce their sulfur and aromatics contents, also causes a reduction in fuel lubricity. Diesel fuels of low lubricity may cause excessive wear of fuel injectors and other moving parts which come in contact with the fuel under high pressures.

Recently, U.S. Pat. No. 5,746,785 in the names of David S. Moulton and David W. Naegeli reported blending a mixture of alkoxy-terminated poly-oxymethylenes, having a varied mixture of molecular weights, with diesel fuel to form an improved fuel for autoignition engines. Two mixtures were produced by reacting paraformaldehyde with (i) methanol or (ii) methylal in a closed system for up to 7 hours and at a temperatures of 150° to 240° C. and pressures of 300 psi to 1,000 psi to form a product containing methoxy-terminated poly-oxymethylenes having a molecular weight of from about 80 to about 350 (polyoxymethylene dimethyl ethers). More specifically, a 1.6 liter cylindrical reactor was loaded with a mixture of methanol and paraformaldehyde, in molar ratio of about 1 mole methanol to 3 moles paraformaldehyde, and in a second preparation, methylal (dimethoxymethane) and paraformaldehyde were combined in a molar ratio of about 1 mole methylal to about 5 moles paraformaldehyde. In the second procedure, a small amount of formic acid, about 0.1% by weight of the total reactants, was added as a catalyst. The same temperatures, pressures and reaction times are maintained as in the first. Disadvantages of these products include the presence of formic acid and thermal instability of methoxy-terminated poly-oxymethylenes under ambient pressure and acidic conditions.

There is, therefore, a present need for catalytic processes to prepare oxygenated organic compounds, particularly polyoxymethylene dimethyl ethers, which do not have the above disadvantages. An improved process should be carried out advantageously in the liquid phase using a suitable condensation-promoting catalyst system, preferably a molecular sieve based catalyst which provides improved conversion and yield. Such an improved process which converts lower value compounds to higher polyoxymethylene dimethyl ethers would be particularly advantageous. Dimethyl ether is, for example, less expensive to produce than methanol on a methanol equivalent basis, and its condensation to polyoxymethylene dimethyl ethers does not produce water as a co-product.

The base diesel fuel,, when blended with such mixtures in a volume ratio of from about 2 to about 5 parts diesel fuel to 1 part of the total mixture, is said to provide a higher quality fuel having significantly improved lubricity and reduced smoke formation without degradation of the cetane number or smoke formation characteristics as compared to the base diesel fuel.

This invention is directed to overcoming the problems set forth above in order to provide Diesel fuel having improved qualities. It is desirable to have a method of producing a high quality diesel fuel that has better fuel lubricity than conventional low-sulfur, low-aromatics diesel fuels, yet has comparable ignition quality and smoke generation characteristics. It is also desirable to have a method of producing such fuel which contains an additional blended component that is soluble in diesel fuel and has no carbon-to-carbon bonds. Furthermore, it is desirable to have such a fuel wherein the concentration of gums and other undesirable products is reduced.

SUMMARY OF THE INVENTION

Economical processes are disclosed for production of a mixture of oxygenated organic compounds which are suitable components for blending into fuel having improved qualities for use in compression ignition internal combustion engines (diesel engines).

According to one aspect of the present invention, there is now provided a continuous process for catalytic production of oxygenated organic compounds, particularly polyoxymethylene dimethyl ethers. More specifically, continuous processes of this invention comprise providing a feedstream comprising methanol, formaldehyde and a soluble condensation promoting component capable of activating a heterogeneous acidic catalyst, and heating the feedstream with the heterogeneous acidic catalyst under conditions of reaction sufficient to form an effluent of condensation comprising water, methanol and one or more polyoxymethylene dimethyl ethers having a structure represented by the formula

in which formula n is a number from 1 to about 10. Advantageously, at least a liquid of the effluent containing polyoxymethylene dimethyl ethers is contacted with an anion-exchange resin to form an essentially acid-free mixture.

Preferably, polyoxymethylene dimethyl ethers useful as components in blending of Diesel fuel have values of n greater than 1. More preferably the mixture of polyoxymethylene dimethyl ethers contains a plurality of polyoxymethylene dimethyl ethers having values of n in a range from 2 to about 7.

Suitable soluble condensation promoting components capable of activating the heterogeneous acidic catalyst comprises at least one member of the group consisting of low boiling, monobasic organic acids, preferably the group consists of formic acid and acetic acid. More preferable soluble condensation promoting component capable of activating the heterogeneous acidic catalyst comprises at least formic acid.

Preferably, the heating of the feedstream with the acidic catalyst is carried out in at least one catalytic distillation column having internal and/or external stages of contact with the acidic catalyst and internal zones to separate methylal from higher polyoxymethylene dimethyl ethers. In a preferred embodiment of the invention at least a liquid portion of the effluent containing polyoxymethylene dimethyl ethers is contacted with an anion exchange resin disposed within a section of the distillation column below the stages of contact with the acidic catalyst to form an essentially acid-free mixture. Advantageously, the essentially acid-free mixture of polyoxymethylene dimethyl ethers is fractionated within a section of the distillation column below the stages of contact with the acidic catalyst to provide an aqueous side-stream which is withdrawn from the distillation column, and an essentially water-free mixture of polyoxymethylene dimethyl ethers having values of n greater than 1 which mixture is withdrawn from the distillation column near its bottom. A source of methanol can be admixed with the feedstream, and/or into the stages of contact with the acidic catalyst.

According to another aspect of the present invention, there is now provided a continuous process for catalytic production of oxygenated organic compounds, particularly polyoxymethylene dimethyl ethers. More specifically, continuous processes of this invention include contacting a source of formaldehyde and a predominately dimethyl ether feedstream comprising dimethyl ether and methanol with a condensation promoting catalyst capable of hydrating dimethyl ether, in a form which is heterogeneous to the feedstream, under conditions of reaction sufficient to form an effluent of the condensation comprising water, methanol, formaldehyde, dimethyl ether, one or more polyoxymethylene dimethyl ethers having a structure represented by the type formula

CH₃O(CH₂O)ₙCH₃ in which formula n is a number from 1 to about 10.

For this aspect of the invention, suitable condensation-promoting catalysts include at least one member of the group consisting of molecular sieves. A preferred class of molecular sieve is crystalline metallosilicates exhibiting the MFI crystal structure, such as crystalline aluminosilicates and crystalline borosilicates. More preferably the molecular sieve is crystalline aluminosilicate exhibiting the MFI crystal structure with a silicon-to-aluminum atomic ratio of at least 10, or the molecular sieve is crystalline borosilicate exhibiting the MFI crystal structure, and has the following compositions in terms of mole ratios of oxides:

0.9±0.2M$_{2/n}$O:B$_2$O$_3$:YSiO$_2$:ZH$_2$O, wherein M is at least one cation having a valence of n, Y is between 4 and about 600, and Z is between 0 and about 160.0.

In another aspect, this invention provides continuous processes which further comprise fractionating the effluent of the condensation to obtain an overhead stream which is predominantly dimethyl ether, and an essentially dimethyl ether-free bottom stream comprising formaldehyde, methanol and at least methylal. Preferably at least a portion of the overhead stream containing dimethyl ether is recycled to contacting with the condensation-promoting catalyst.

According to a further aspect of this invention, the essentially dimethyl ether-free bottom stream comprising formaldehyde, methanol and at least methylal is heated with an acidic catalyst, which is heterogeneous to the feedstream, under conditions of reaction sufficient to convert formaldehyde and methanol present to methylal and higher polyoxymethylene dimethyl ethers.

Preferably, the heating of the bottom stream with the acidic catalyst employs at least one catalytic distillation column with internal and/or external stages of contact with the acidic catalyst, and internal zones to separate the methylal from the higher polyoxymethylene dimethyl ethers.

Suitable acidic catalysts include at least one member of the group consisting of bentonites, montmorillonites, cation-exchange resins, and sulfonated fluoroalkylene resin derivatives, preferably comprises a sulfonated tetrafluoroethylene resin derivative. A preferred class of acidic catalysts comprises at least one cation-exchange resin of the group consisting of styrene-divinylbenzene copolymers, acrylic acid-divinylbenzene copolymers, and methacrylic acid-divinylbenzene copolymers. Preferably, the heating of the bottom stream with the acidic catalyst employs at least one distillation column with internal and/or external stages of contact with the acidic catalyst.

Advantageously, the mixture of polyoxymethylene dimethyl ethers is contacted with an anion exchange resin to form an essentially acid-free mixture. Contacting with the anion exchange resin is preferably carried out within a section of the catalytic distillation column below the stages of contact with the acidic catalyst to form an essentially acid-free mixture.

In a preferred embodiment of the invention the essentially acid-free mixture of polyoxymethylene dimethyl ethers is fractionated within a section of the distillation column below the stages of contact with the acidic catalyst to provide an aqueous side-stream which is withdrawn from the distillation column, and an essentially water-free mixture of higher molecular weight polyoxymethylene dimethyl ethers (values of n greater 1) which is withdrawn from the distillation column near its bottom. Advantageously, at least a portion of the aqueous side-stream is used for recovery of an aqueous formaldehyde solution in an adsorption column.

In another aspect, this invention is an integrated process wherein the source of formaldehyde is formed by a process comprising continuously contacting a gaseous feedstream comprising dimethyl ether, dioxygen and diluent with a catalytically effective amount of an oxidation promoting catalyst comprising tungsten oxide as an essential catalyst component at elevated temperatures to form a gaseous mixture comprising formaldehyde, dimethyl ether, dioxygen, diluent, carbon monoxide, carbon dioxide and water vapor. The gaseous mixture is cooled to predominantly condense water and adsorb formaldehyde therein. The resulting aqueous liquid is the source of formaldehyde which is separated from a mixture of gases comprising dioxygen, diluent, carbon monoxide, carbon dioxide and water vapor.

At least a portion of the mixture of gases separated from the resulting aqueous source of formaldehyde is recycled into the gaseous feedstream.

For this aspect of the invention, suitable oxidation-promoting catalysts include tungsten oxide and optionally up to about 8 percent by weight of a compound selected from the group consisting of oxides of boron, phosphorous, vanadium, selenium, molybdenum and bismuth, phosphoric acid, ammonium phosphate and ammonium chloride. A preferred class of oxidation-promoting catalysts comprises tungsten oxide and optionally up to about 5 percent by weight of a compound selected from the group consisting of phosphoric acid and ammonium phosphate.

Preferably the formaldehyde formed is recovered as an aqueous solution containing less than about 60 percent water, preferably less than about 50 percent water and more preferably less than about 25 percent water by using at least one continuous adsorption column with cooling to temperatures in a range downward from about 100° C. to 25° C.

Suitable sources of dioxygen are air or a dioxygen-enriched gas stream obtained by physically separating a gaseous mixture containing at least about 10 volume percent dioxygen into a dioxygen-depleted stream and a dioxygen-enriched gas stream. Preferably the gaseous mixture contains at least 60 volume percent dinitrogen and wherein the dioxygen-enriched gas stream comprises a volume ratio of dinitrogen to dioxygen of less than 2.5 to 1.

For a more complete understanding of the present invention, reference should now be made to the embodiments illustrated in greater detail in the accompanying drawing and described below by way of examples of the invention.

GENERAL DESCRIPTION

Figure 1:
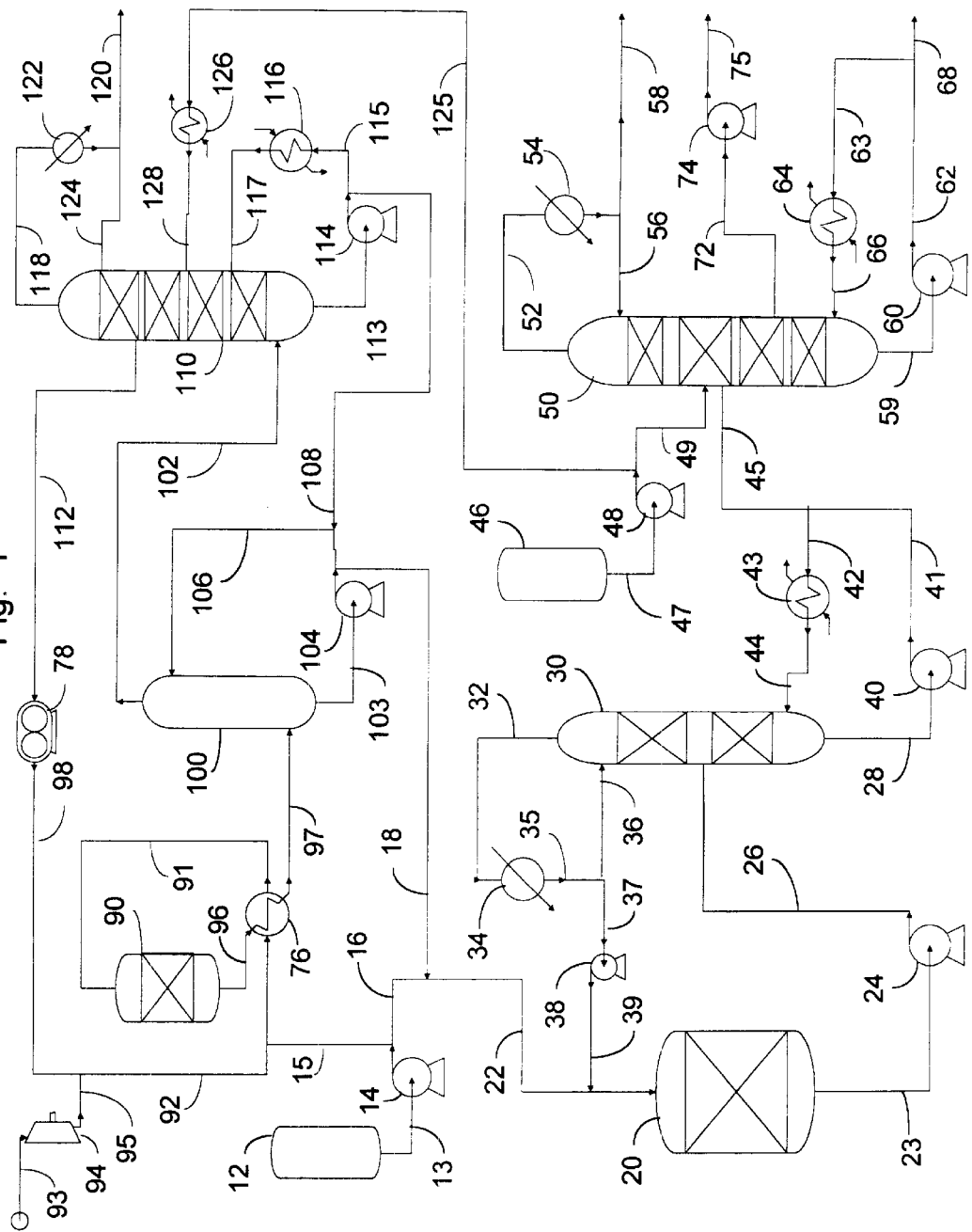
FIG. 1 is a schematic flow diagram depicting a preferred aspect of the present invention for continuous catalytic production of polyoxymethylene dimethyl ethers by chemical conversion of dimethyl ether and formaldehyde in which unreacted dimethyl ether is recovered from the effluent for recycling, and a resulting dimethyl ether-free liquid mixture is heated in a catalytic distillation column with internal stages of contact to convert formaldehyde and methanol present to methylal and higher polyoxymethylene dimethyl ethers. This reaction mixture is contacted with an anion exchange resin to form an essentially acid-free product mixture and fractionated to provide suitable components for blending into diesel fuel. The source of formaldehyde in the integrated process depicted in FIG. 1 is a stream of aqueous formaldehyde in methanol derived from oxidation of dimethyl ether. In this aspect of invention, recycle gas from the formaldehyde absorber is combined with air, mixed with dimethyl ether, preheated against reactor product, and then fed to the formaldehyde reactor.

In one class of preferred embodiments, improved processes of the present invention employ a feedstream comprising methanol, formaldehyde and a soluble condensation promoting component capable of activating a heterogeneous acidic catalyst. Suitable components include any acidic compound soluble in the feedstream, preferably an organic compound soluble in a feedstream of about 30 to about 85 percent by weight formaldehyde in methanol solution containing less than 5 percent water.

In this class, preferred condensation promoting components capable of activating a heterogeneous acidic catalyst include members of the group consisting of low boiling, monobasic organic acids, more preferably acetic acid and/or formic acid.

Improved processes of the present invention may also or alternatively employ a heterogeneous, condensation promoting catalyst capable of hydrating dimethyl ether in conversion of dimethyl ether and formaldehyde to form a condensation effluent. In general, after the feedstream is passed over the catalyst it will contain a mixture of organic oxygenates at least one of which is of higher molecular weight than the starting dimethyl ether. For example, effluent mixtures can comprise water, methanol, formaldehyde, dimethyl ether, methylal and other polyoxymethylene dimethyl ethers having a structure represented by the formula $$CH_3O(CH_2O)_nCH_3$$

in which formula n is a number ranging between 1 and about 15, preferably between 1 and about 10. More preferably the mixture contains a plurality of polyoxymethylene dimethyl ethers having values of n in a range from 2 to about 7. Conditions of reaction include temperatures in a range from about 50° to about 300° C., preferably in a range from about 150° to about 250° C.

Stoichiometry of this condensation may be expressed by the following equations;

$$CH_3OCH_3 + nCH_2O \rightleftharpoons CH_3O(CH_2O)_nCH_3$$
$$2CH_3OH + mCH_2O \rightleftharpoons CH_3O(CH_2O)_mCH_3 + H_2O$$

which may be combined as in the following equation when n is equal to m;

$$CH_3OCH_3 + 2CH_3OH + 2nCH_2O \rightleftharpoons 2CH_3O(CH_2O)_nCH_3 + H_2O$$

As shown above, the synthesis of methylal and higher polyoxymethylene dimethyl ethers from dimethyl ether, methanol, and formaldehyde is a reversible reaction that yields water as a co-product. Under certain conditions at least a portion of the water may be consumed in a dehydrogenation reaction expressed by the following equations;

$$CH_3OCH_3 + CH_3OH + H_2O \rightarrow 3CH_2O + 3H_2$$

and $$CH_3OCH_3 + H_2O \rightleftharpoons 2CH_3OH$$

Sources of dimethyl ether useful herein are predominantly dimethyl ether, preferably at least about 80 percent dimethyl ether by weight, and more preferably about 90 percent dimethyl ether by weight. Suitable dimethyl ether sources may contain other oxygen containing compounds such as alkanol and/or water, preferably not more than about 20 percent methanol and/or water by weight, and more preferably not more than about 15 percent methanol and/or water by weight.

The process can be performed at any temperature and pressure at which the reaction proceeds. Preferred temperatures are between about 20° and about 150° C., with between about 90° and about 125° C. being more preferred. The most preferred temperatures are between about 115° and about 125° C.

According to this aspect of the present invention, the ratio of formaldehyde to dimethyl ether in the feedstreams is any mole ratio which results in the production of the desired oxygenated organic compound. The ratio of formaldehyde to dimethyl ether is preferably between about 10:1 and about 1:10 moles. The ratio of formaldehyde to dimethyl ether is preferably between about 5:1 and about 1:5 moles. More preferably, the ratio of formaldehyde to dimethyl ether is between about 2:1 and about 1:2 moles.

The pressure can be atmospheric or super-atmospheric pressure. Preferred pressures are, according to the present invention, between about 1 and about 100 atmospheres, with between about 15 and about 25 atmospheres being most preferred.

The reaction mixture feed gas flow rate, expressed as gas hourly space velocity, can be between about 50 and about 50,000 hr$^{-1}$, most preferably, between about 100 and about 2,000 hr$^{-1}$. The diethyl ether can be recovered from the mixture by methods well known in the art. One particularly desirable method is the use of distillation of the condensed product.

The process of this invention can be performed in either a fixed or fluid bed reactor, using either continuous or batch processing methods. It is preferred to use a fixed bed reactor and a continuous mode of operation.

Broadly, according to the present invention, a catalyst system is provided which comprises at least one molecular sieve, preferably a crystalline metallosilicate exhibiting the MFI crystal structure. Generally the crystalline metallosilicate is combined with active or inactive materials, synthetic or naturally occurring zeolites, as well as inorganic or organic materials which would be useful for binding the crystalline metallosilicate. Other well-known materials include mixtures of silica, silica-alumina, alumina sols, clays, such as bentonite or kaolin, or other binders well known in the art. The crystalline metallosilicate can also be mixed intimately with porous matrix materials, such as silica-magnesia, silica-alumina, silica-thoria, or silica-titania. The crystalline metallosilicate content can vary anywhere from a few up to 100 percent by weight of the total finished product. Typical catalytic compositions contain about 5 percent to about 80 percent by weight of the crystalline metallosilicate Generally, the term "molecular sieve" includes a wide variety of positive ion-containing crystalline materials of both natural and synthetic varieties. They are generally characterized as crystalline aluminosilicates, although other crystalline materials are included in the broad definition. The crystalline aluminosilicates are made up of networks of tetrahedra of $SiO_4$ and $AlO_4$ moieties in which the silicon and aluminum atoms are cross-linked by the sharing of oxygen atoms. The electrovalence of the aluminum atom is balanced by the use of positive ions such as alkali metal or alkaline earth metal cations.

Zeolitic materials useful herein, both natural and synthetic, have been demonstrated in the past to have catalytic capabilities for many hydrocarbon processes. Zeolitic materials, often referred to as molecular sieves, are ordered porous crystalline aluminosilicates having a definite structure with large and small cavities interconnected by channels. The cavities and channels throughout the crystalline material are generally uniform in size allowing selective separation of hydrocarbons. Consequently, these materials in many instances have come to be classified in the art as molecular sieves and are utilized, in addition to the selective adsorptive processes, for certain catalytic properties. The catalytic properties of these materials are also affected, to some extent, by the size of the molecules which are allowed selectively to penetrate the crystal structure, presumably to be contacted with active catalytic sites within the ordered structure of these materials.

Manufacture of the ZSM materials utilizes a mixed base system in which sodium aluminate and a silicon-containing material are mixed together with sodium hydroxide and an organic base, such as tetrapropylammonium hydroxide and tetrapropylammonium bromide, under specified reaction conditions to form the crystalline aluminosilicate.

A preferred class of useful molecular sieves, according to the present invention, are crystalline borosilicate molecular sieves disclosed in commonly assigned U.S. Pat. Nos. 4,268,420, 4,269,813, 4,292,457, and 4,292,458 to Marvin R. Klotz, which are incorporated herein by reference.

Suitable for use according to the present invention are, broadly, crystalline borosilicates which comprise a molecular sieve material having the following compositions in terms of mole ratios of oxides:

where M is at least one cation having a valence of n, Y is between 4 and about 600, and Z is between 0 and about 160.

Embodiments of such borosilicate provide an X-ray diffraction pattern comprising the following X-ray diffraction lines:

| d (Å) | Assigned Strength |
|---|---|
| 11.2 ± 0.2 | W–VS |
| 10.0 ± 0.2 | W–MS |
| 5.97 ± 0.07 | W–M |
| 3.82 ± 0.05 | VS |
| 3.70 ± 0.05 | MS |
| 3.62 ± 0.05 | M–MS |
| 2.97 ± 0.02 | W–M |
| 1.99 ± 0.02 | VW–M | wherein the assigned strengths correspond to the following values of relative peak heights:

| Assigned Strength | Relative Peak Height |
|---|---|
| VW | less than 10 |
| W | 10–19 |
| M | 20–39 |
| MS | 40–70 |
| VS | greater than 70 | and "d" represents interplanar spacings, expressed in terms of Angstrom units. A range of assigned strengths comprises all strengths between the limits shown.

Embodiments of these borosilicates are prepared by the method which comprises: (1) preparing a mixture containing an oxide of silicon, an oxide of boron, a hydroxide of an alkali metal or an alkaline earth metal, an alkyl ammonium cation or a precursor of an alkyl ammonium cation, and water; and (2) maintaining said mixture at suitable reaction conditions to effect formation of said borosilicate, said reaction conditions comprising a reaction temperature within the range of about 25° to about 300° C., a pressure of at least the vapor pressure of water at the reaction temperature, and a reaction time that is sufficient to effect crystallization.

After recovering a dimethyl ether-free mixture form the condensation effluent, the mixture is heated in a catalytic distillation column with an acidic catalyst, which is heterogeneous to the feedstream, under conditions of reaction sufficient to convert formaldehyde and methanol present to methylal and higher polyoxymethylene dimethyl ethers. Examples of the solid acidic catalyst for use in the present invention include cation exchange resins, sulfonated fluoroalkylene resin derivatives, and crystalline aluminosilicates.

Cation exchange resins that can be used in the present invention may be carboxylated or sulfonated derivatives, but sulfonated derivatives are preferred because of the high reaction yield that can be attained. Ion exchange resins that can be used may be gel-type cation exchange resins or macroporous (macroreticular) cation-exchange resins, but the latter as exemplified by Amberlite 200° C. of Organic Co, Ltd. and Lewalit SP112 of Bayer A. G. are preferred because of the high reaction yield that can be attained. Specific examples of useful ion exchange resins include a styrene-divinylbenzene copolymer, an acrylic acid-divinylbenzene copolymer, a methacrylic acid-divinylbenzene copolymer, etc.

A sulfonated tetrafluoroethylene resin derivative (trade name, Naflon H) is preferably used as a sulfonated fluoroalkylene resin derivative.

The most desirable of these solid acidic catalysts are macroreticular cation exchange resins having sulfonate groups.

According to an integrated process of the invention a source of formaldehyde is formed by subjecting dimethyl ether in the vapor phase to hydration and oxidation in the presence a catalytically effective amount of an oxidation promoting catalyst comprising tungsten oxide as an essential catalyst component at elevated temperatures to form a gaseous mixture comprising formaldehyde, dimethyl ether, dioxygen, diluent, carbon monoxide, carbon dioxide and water vapor; cooling the gaseous mixture to predominantly condense water and adsorb formaldehyde therein; and separating the resulting aqueous source of formaldehyde from a mixture of gases comprising dioxygen, diluent, carbon monoxide, carbon dioxide and water vapor.

According to this aspect of the present invention, the ratio of dioxygen to total dimethyl ether is, according to the present invention, any mole ratio which results in the production of the desired source of formaldehyde. The ratio of dioxygen to ether and, if present, alkanol is preferably between about 1:1 and about 1:1000 moles. More preferably, the ratio of dioxygen to dimethyl ether is between about 1:1 and about 1:100 moles. Most preferably, the ratio of dioxygen to dimethyl ether is between about 1:1 and about 1:10 moles.

Operating conditions of reaction usually fall in the following ranges:

Dimethyl ether: 1 mol percent up to 17.4 mol percent
Air: 99 mol percent to 82.6 mol percent
Reaction temperature: 200° to 450° C.
Space velocity: 1,000–20,000 hr$^{-1}$ Preferable conditions are as follows:

Dimethyl ether: 3 mol percent to 12 mol percent
Reaction temperature: 250° to 400° C.
Space velocity: 1,000–10,000 hr$^{-1}$ The dioxygen can be added to the reaction mixture as pure molecular oxygen, or diluted with an inert gas such as nitrogen or argon. It is preferred to keep the dioxygen at no more than 10 mole percent of the entire reaction feed so as to avoid the formation of explosive mixtures.

According to the present invention, within the oxidation reaction zone dimethyl ether is oxidized with a source of dioxygen in the presence of an oxidation-promoting catalytic composition containing, as an essential ingredient, an metal oxide with or without up to about 10 percent of a supplemental inorganic compound based upon the total weight of metal oxide and supplemental inorganic compounds Suitable metal oxide catalysts have been developed for reacting dimethyl ether with a source of dioxygen to produce formaldehyde, as described in U.S. Pat. Number 3,655,771, or U.S. Pat. No. 4,753,916 which patents are specifically incorporated herein in their entirety by reference.

Well known methods of preparing suitable tungsten oxide include adding to ammonium tungstate concentrated hydrochloric or nitric acid, to precipitate the oxide. Oxide is molded into tablets or supported on inert carriers, such as alumina, Carborundum, pumice or the like. Advantageously, vanadium oxide, boron oxide, molybdenum oxide, phosphoric acid, an ammonium salt thereof, ammonium chloride or the like is added to tungsten oxide in an amount of not more than 10%, in order to maintain the activity of tungsten oxide at the original level and to obtain a catalyst having a sufficient mechanical strength to withstand operating conditions during its useful catalytic life. The addition thereof results in the combination with tungsten oxide and consequently the aggregatability of powdered tungsten oxide is enhanced, molding of the oxide is facilitated and the oxide is hardened.

For example, 5 percent by weight of phosphoric acid is added to tungsten oxide powder, produced by any generally known method, and the resulting mixture is milled well with water into a paste. This paste is dried, ground into 12 mesh, size-controlled and shaped into tablets by a tablet-forming machine. These tablets are sufficiently dried, and thereafter calcined in air at 500° C. for 7 to 8 hours to obtain very hard tablets.

The present invention further provides a method for selective oxidation of dimethyl ether to formaldehyde in the presence of an catalytically effective amount of a composition of matter comprising $\beta\text{-Mo}_{(1-x)}W_xO_3$, where x is a number between 0 and 1, preferably where x is a number between 0 and 0.5, and more preferably where x is 0 or a number between 0 and 0.1. Using such catalytic material, the selective oxidation of dimethyl ether to formaldehyde is conducted at temperatures in a range from about 200° to about 450° C., and more preferably in a range from about 250° to about 400° C. Preferred operating pressures are from about 1 to about 100 kPa, and more preferably from about 6 to about 15 kPa.

One method for preparation of a composition comprising $\beta\text{-Mo}_{(1-x)}W_xO_3$, comprises spray-drying a solution of molybdic acid or molybdic and tungstic acids in appropriate concentrations and heating the resulting powder at a temperature of from about 275° to about 450°C. Another method comprises sputtering a molybdenum or mixed metal oxide target in appropriate concentrations onto a thermally floating substrate in an atmosphere comprising oxygen and an inert gas wherein the oxygen is in an amount from about 5 to about 50 volume percent.

Most preferred compositions comprising $\beta\text{-Mo}_{(1-x)}W_xO_3$, are where x is 0 or a number between 0 and 0.05. This phase of the specified metal or mixed metal oxide has a distorted three dimensional $RCO_3$ structure based on corner-linked octahedra. The thermal stability of the beta phase of $MoO_3$, can be improved by tungsten substitution as evidenced by the beta to alpha transformation temperature of about 530° C. of $Mo_{0.95}W_{x0.5}O_3$, compared to about 450° C of $MoO_3$.

Another method for preparation of a composition comprising the "beta" phase of the specified metal and mixed metal oxides ($\beta\text{-Mo}_{(1-x)}W_xO_3$) can be prepared in films by sputtering or spin coating.

In the present method, dimethyl ether may be used alone, or methanol and dimethyl ether can be used in admixture with each other to produce formaldehyde.

DESCRIPTION OF THE PREFERRED EMBODIMENTS

In order to better communicate the present invention, still another preferred aspect of the invention is depicted schematically in FIG. 1. Referring now to FIG. 1, a mixture containing dimethyl ether in substantially liquid form is unloaded, for example from a road tanker (not shown), into dimethyl ether storage vessel 12 which supplies charge pump 14 through conduit 13. Charge pump 14 transfers the liquid dimethyl ether from storage vessel 12 into catalytic reactor 20 through conduit 16 and manifold 22. Aqueous formaldehyde in methanol is supplied to manifold 22 through conduit 18, and into catalytic reactor 20. Catalytic reactor 20 contains a catalyst which has a condensation-promoting action and is capable of hydrating dimethyl ether. Preferred catalysts are based upon a suitable molecular sieve.

It should be apparent that effluent from the catalytic reactor is a valuable product in itself. A portion of the stream can optionally be diverted from catalytic reactor 20 for delivery to a destination (not shown) where stream may subsequently be separated to recover, for example, dimethyl ether, formaldehyde, methylal and/or other polyoxymethylene dimethyl ethers. The stream can alternatively be utilized as a source of feed stock for chemical manufacturing.

The effluent stream from catalytic reactor 20 is transferred through conduits 23 and 26, by means of pump 24, and into ether recovery column 30, where unreacted dimethyl ether is separated from the effluent stream to form a resulting liquid mixture of condensation products containing any unreacted formaldehyde. A dimethyl ether fraction is taken overhead through conduit 32 and into condenser 34 where a liquid condensate is formed. A suitable portion of the liquid condensate is refluxed into column 30 through conduits 35 and 36 while another portion of the condensate is supplied to manifold 22 through conduits 37 and 39, by means of pump 38, and into catalytic reactor 20.

Conduit 28 supplies pump 40 with liquid from the bottom of column 30. A suitable portion of the liquid stream from the bottom of column 30 is transferred through conduits 41 and 42, by means of pump 40, and into reboiler 43 which is in flow communication with the bottom of the column through conduit 44. A liquid stream from the bottom of column 30 is transferred through conduit 45 into reactive distillation column 50, where simultaneous chemical reaction and multicomponent distillation are carried out coextensively in the same high efficiency, continuous separation apparatus. Optionally, a stream containing methanol from storage vessel 46 may by fed into the reactive distillation column 50. Charge pump 48 transfers methanol in substantially liquid form into the reactive distillation column 50 through conduits 47 and 49.

Solid acidic catalyst is present in the reactive distillation column 50 to allow solutions containing water, methanol, formaldehyde, methylal and one or more other polyoxymethylene dimethyl ethers to be brought into solid-liquid contact counter-currently with the catalyst to form products including methylal and higher molecular weight polyoxymethylene dimethyl ethers. More volatile reaction products are taken overhead from the high efficiency separation apparatus, whereas water and less volatile reaction products are carried down the high efficiency separation apparatus.

The overhead vapor stream from reactive distillation column 50 is transferred through conduit 52 into condenser 54. A suitable portion of condensate from condenser 54 is refluxed into reactive distillation column 50 through conduits 55 and 56. A product stream containing methylal is transferred through conduit 58 to product storage (not shown). Conduit 59 supplies pump 60 with liquid containing higher molecular weight polyoxymethylene dimethyl ethers from the bottom of column 50. A suitable portion of liquid from the bottom of column 50 is transferred, by means of pump 60, through conduits 62 and 63 into reboiler 64 which is in flow communication with the bottom of the column by means of conduit 66. A product stream containing higher molecular weight polyoxymethylene dimethyl ethers is transferred through conduit 68 to product storage (not shown). Preferably, an anion exchange resin disposed within a section of the distillation column below the stages of contact with the acidic catalyst to form an essentially acid-free mixture.

An aqueous side stream containing low levels of unreacted formaldehyde and/or methanol is discharged from column 50 through conduit 72. The side stream from column 50 is transferred by means of pump 74 through conduit 75 to waste disposal (not shown).

In the formaldehyde preparation aspect of the invention which is described herein below, a gaseous feedstream comprising dimethyl ether, dioxygen and diluent is contacted with a catalytically effective amount of an oxidation promoting catalyst comprising tungsten oxide as an essential catalyst component. In this embodiment of invention, recycle gas from the formaldehyde absorber is combined with air, mixed with dimethyl ether, preheated against reactor product, and then fed to the formaldehyde reactor.

Referring now to the upper portion of FIG. 1, a mixture containing dimethyl ether in substantially liquid form is supplied from dimethyl ether storage vessel 12 to pump 14 through conduit 13, and into feed manifold 92 through conduit 15. By means of blower 78 a recycle stream of wet gas is transferred into feed manifold 92 through conduit 98. A gaseous stream containing dioxygen and dinitrogen from a source (not shown) is supplied to compressor 94 through conduit 93. Compressed gas is transferred through conduit 95, combined in feed manifold 92 with the recycle stream of wet gas from the formaldehyde adsorber and the dimethyl ether. The resulting feed mixture is heated against reactor effluent in heat exchanger 76, and transferred into oxidation reactor 90 through conduit 91.

The mole ratio of fresh air feed to dimethyl ether is about 3.5, and the mole ratio of recycled gas to fresh air feed is about 2.1. Oxidation reactor 90 is a vertical heat exchanger. The tubes are filled with catalyst pellets. (The upper and lower regions of the tubes contain pellets of inert material.) Typically, a portion of heat generated in the catalyst bed is diverted to steam generation within oxidation reactor 90 thereby providing cooling of effluent from the bed (not shown). A thermal fluid is vaporized on the shell side and circulated to a steam generator to generate steam at pressures of up to 300 psig.

Within the oxidation reaction zone of reactor 90 is an oxidation-promoting catalyst, preferably consisting essentially of a metal oxide component with or without a supplemental inorganic compound. In a preferred embodiment on this invention, tungsten oxide catalysts are used because they give almost complete oxidation to formaldehyde at much lower temperatures than are required for the silver-catalyzed dehydrogenation reaction.

In this embodiment of the invention, tungsten oxide catalyzes the conversion of dimethyl ether to formaldehyde by an oxidation reaction at temperatures in a range from about 350° to about 600° C., preferably in a range from about 400° to about 500° C.:

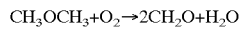

$$CH_3OCH_3 + O_2 \rightarrow 2CH_2O + H_2O$$

In this case, a large excess of air is necessary to obtain maximum yields and to avoid explosive feed concentrations. Some flexibility exists in the explosive limits, depending upon the temperature, pressure, and normal moisture content of the air. However, normal practical limitations appear to set a lower boundary between 8 mol percent and 10 mol percent in the reactor feed.

Several side reactions occur, especially those producing carbon monoxide, formic acid, and dimethyl ether. However, because of a lower reaction temperature, the extent of these reactions is smaller than in the silver-catalyzed process.

Gaseous effluent from oxidation reactor 90 is transferred through conduit 96, cooled against the reactor feedstream in exchanger 76 and then passed through conduit 97 into spray column 100 where a solution of aqueous formaldehyde in methanol is formed. Formaldehyde solution from the bottom of spray column 100, at temperatures in a range downward from about 100° C. to about 75° C., is supplied to pump 104 through conduit 103. As previously described, a portion of the aqueous formaldehyde in methanol is transferred through conduit 18 and manifold 22 into catalytic reactor 20. Formaldehyde solution from the spray column is generally from about 30 to about 85 percent by weight formaldehyde in methanol solution containing less than about 5 percent water and less than 350 ppm of formic acid. Another portion of the aqueous formaldehyde solution is combined with a crude solution of formaldehyde in methanol, supplied from the bottom adsorption column 110 through conduits 113 and 108, by means of pump 114. The combination forms a stream which is circulated to the top of spray column 100 through conduit 106. It is important to maintain the temperature of the pump-around stream above about 70° C. to prevent paraformaldehyde formation. Optionally, a portion of the cooling required in spray column 100 may be obtained by including a heat exchanger in the flow through conduit 106.

A gaseous overhead stream from spray column 100 is transferred through conduit 102 into adsorption column 110, which contains a high efficiency packing or other means for contacting counter-currently the gaseous stream with aqueous adsorption liquid. A crude solution of formaldehyde in methanol from the bottom of adsorption column 110 is circulated in a pump-around to a lower section of the column through conduits 113 and 115, cooler 116, and conduit 117 by means of pump 114.

As needed, methanol for the adsorption is supplied to a section of adsorption column 110 by means of pump 48 through conduit 125, cooler 126, and conduit 128. Further up the column, pump-arounds may be cooled to successively lower temperatures. In some configurations, the lower pump-around stream is not cooled at all.

A vapor side draw from adsorption column 110 is transferred through conduit 112 and mixed with fresh air as previously described. The adsorber overhead passes through conduit 118 into condenser 122. An appropriate amount of condensate is formed and refluxed to the top section of the adsorber column through conduit 124. Overhead temperatures in adsorption column 110 are in a range of about 15° to about 55° C., preferably about 30° to about 40° C. Gases are vented from condenser 122 through conduit 120 to disposal, typically, in a thermal oxidation unit (not shown).

The absorber overhead, which contains trace amounts of formaldehyde (about 10–30 ppm), is treated in several ways by catalytic or thermal converter to oxidize hydrocarbons and recuperative heat exchange. Typically, 170 psig to 200 psig steam is generated to improve overall economics of preferred embodiments of the invention.

Figure 2:
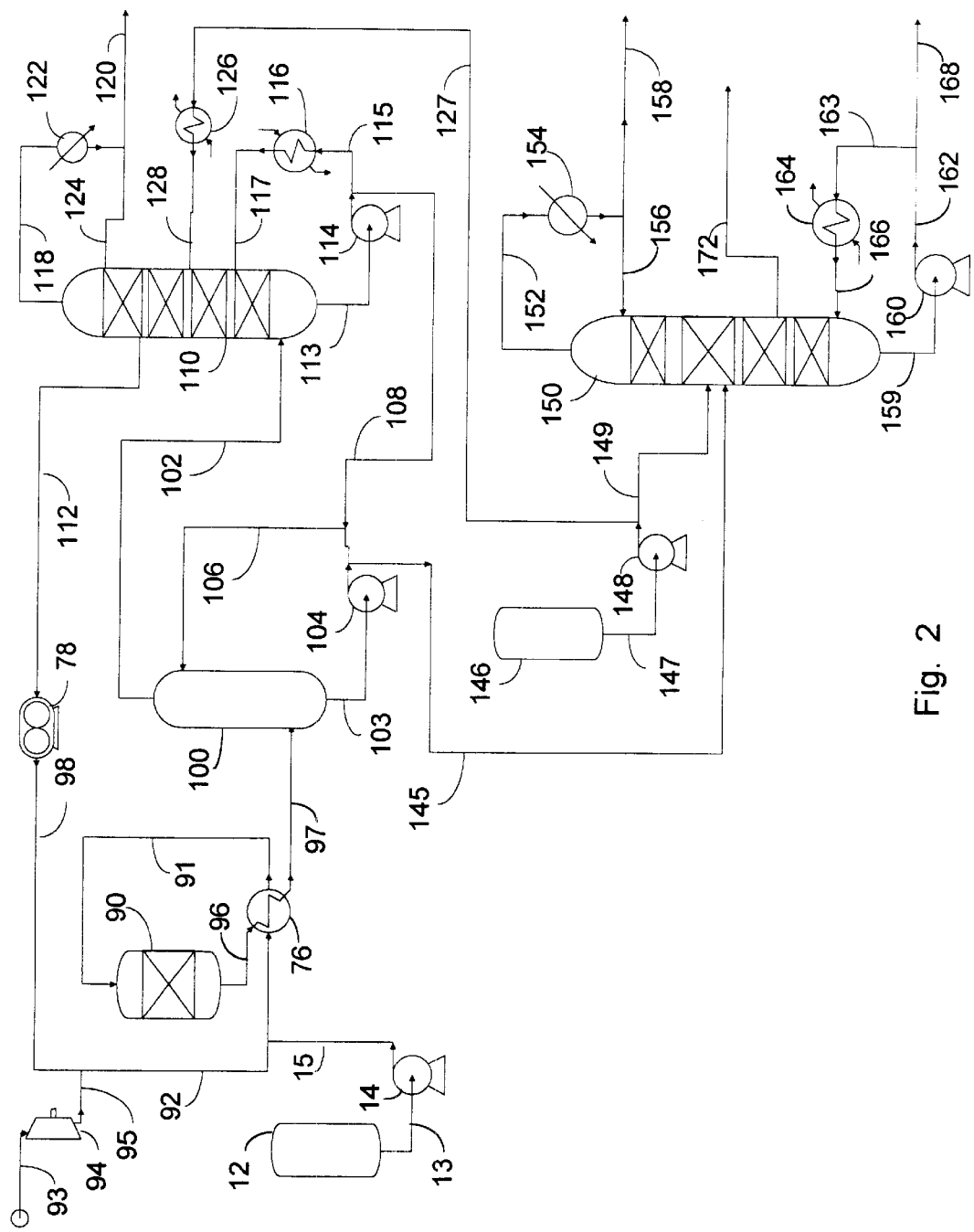
FIG. 2 is a schematic flow diagram depicting a preferred aspect of the present invention for continuous catalytic production of polyoxymethylene dimethyl ethers by chemical conversion of methanol and formaldehyde in which a feedstream comprising a soluble condensation promoting component capable of activating a heterogeneous acidic catalyst is heated with the heterogeneous acidic catalyst in a catalytic distillation column with internal stages of contact. A liquid portion of the effluent of condensation, containing polyoxymethylene dimethyl ethers, is contacted with an anion exchange resin disposed within a section of the distillation column below the stages of contact with the acidic catalyst to form an essentially acid-free mixture, and fractionated to provide suitable components for blending into diesel fuel. The feedstream in the integrated process depicted in FIG. 2 is again a stream of aqueous formaldehyde in methanol derived from oxidation of dimethyl ether. In this aspect of invention, recycle gas from the formaldehyde absorber is combined with air, mixed with dimethyl ether, preheated against reactor product, and then fed to the formaldehyde reactor.

Another preferred aspect of the invention is depicted schematically in FIG. 2. In this integrated process a feedstream comprising methanol, formaldehyde and a soluble condensation promoting component capable of activating a heterogeneous acidic catalyst is provided by contacting dimethyl ether in the vapor phase with a catalytically effective amount of an oxidation promoting catalyst comprising tungsten oxide as an essential catalyst component at elevated temperatures to form a gaseous mixture comprising formaldehyde, dimethyl ether, dioxygen, diluent, carbon monoxide, carbon dioxide and water vapor; cooling the gaseous oxidation mixture with an adsorption liquid and adsorbing formaldehyde therein; and separating the resulting liquid source of formaldehyde from a mixture of gases comprising dioxygen, diluent, carbon monoxide, carbon dioxide and water vapor.

Referring now to the upper portion of FIG. 1, a mixture containing dimethyl ether in substantially liquid form is supplied from dimethyl ether storage vessel 12 to pump 14 through conduit 13, and into feed manifold 92 through conduit 15. By means of blower 78 a recycle stream of wet gas is transferred into feed manifold 92 through conduit 98. A gaseous stream containing dioxygen and dinitrogen from a source (not shown) is supplied to compressor 94 through conduit 93. Compressed gas is transferred through conduit 95, combined in feed manifold 92 with the recycle stream of wet gas from the formaldehyde adsorber and the dimethyl ether. The resulting feed mixture is heated against reactor effluent in heat exchanger 76, and transferred into oxidation reactor 90 through conduit 91.

The mole ratio of fresh air feed to dimethyl ether is about 3.5, and the mole ratio of recycled gas to fresh air feed is about 2.1. Oxidation reactor 90 is a vertical heat exchanger. The tubes are filled with catalyst pellets. (The upper and lower regions of the tubes contain pellets of inert material.) Typically, a portion of heat generated in the catalyst bed is diverted to steam generation within oxidation reactor 90 thereby providing cooling of effluent from the bed (not shown). A thermal fluid is vaporized on the shell side and circulated to a steam generator to generate steam at pressures of up to 300 psig.

Within the oxidation reaction zone of reactor 90 is an oxidation-promoting catalyst, preferably consisting essentially of a metal oxide component with or without a supplemental inorganic compound. In a preferred embodiment on this invention, tungsten oxide catalysts are used because they give almost complete oxidation to formaldehyde at much lower temperatures than are required for the silver-catalyzed dehydrogenation reaction.

Gaseous effluent from oxidation reactor 90 is transferred through conduit 96, cooled against the reactor feedstream in exchanger 76 and then passed through conduit 97 into spray column 100 where a solution of aqueous formaldehyde in methanol is formed. Formaldehyde solution from the bottom of spray column 100, at temperatures in a range downward from about 100° C. to about 75° C., is supplied to pump 104 through conduit 103. Formaldehyde solution from the spray column is generally from about 30 to about 85 percent by weight formaldehyde in methanol solution containing less than about 5 percent water and less than 350 ppm of formic acid.

It should be apparent that effluent from the spray column is a valuable product in itself. A portion of the stream can optionally be diverted from adsorption tower 100 for delivery to a destination (not shown) where the stream may subsequently be separated to recover, for example, formaldehyde and methanol and/or dimethyl ether. The stream can alternatively be utilized as a source of feed stock for chemical manufacturing.

The formaldehyde solution from pump 104 is combined with a solution of formaldehyde in methanol supplied from the bottom of adsorption column 110 through conduits 113 and 108, by means of pump 114. The combination forms a stream which is circulated to the top of spray column 100 through conduit 106. It is important to maintain the temperature of the pump-around stream above about 70° C. to prevent paraformaldehyde formation. Optionally, a portion of the cooling required in spray column 100 may be obtained by including a heat exchanger in the flow through conduit 106.

A gaseous overhead stream from spray column 100 is transferred through conduit 102 into adsorption column 110, which contains a high efficiency packing or other means for contacting counter-currently the gaseous stream with aqueous adsorption liquid. A solution of formaldehyde in methanol from the bottom of adsorption column 110 is circulated in a pump-around to a lower section of the column through conduits 113 and 115, cooler 116, and conduit 117 by means of pump 114.

As needed, methanol for the adsorption is supplied to a section of adsorption column 100 by means of pump 148 through conduit 127, cooler 126, and conduit 128. Further up the column, pump-arounds may be cooled to successively lower temperatures. In some configurations, the lower pump-around stream is not cooled at all.

A vapor side draw from adsorption column 110 is transferred through conduit 112 and mixed with fresh air as previously described. The adsorber overhead passes through conduit 118 into condenser 122. An appropriate amount of condensate is formed and refluxed to the top section of the adsorber column through conduit 124. Overhead temperatures in adsorption column 110 are in a range of about 15° to about 55° C., preferably about 30° to about 40° C. Gases are vented from condenser 122 through conduit 120 to disposal, typically, in a thermal oxidation unit (not shown). The absorber overhead, which contains trace amounts of formaldehyde (about 10–30 ppm), is treated in several ways by catalytic or thermal converter to oxidize hydrocarbons and recuperative heat exchange. Typically, 170 psig to 200 psig steam is generated to improve overall economics of preferred embodiments of the invention.

A portion of the solution of formaldehyde in methanol is diverted from pump 104 into reactive distillation column 150 through conduit 145. In reactive distillation column 150 simultaneous chemical reaction and multicomponent distillation are carried out coextensively in the same high efficiency, continuous separation apparatus. Optionally, a stream containing methanol from storage vessel 146 may by fed into the reactive distillation column 150. Charge pump 148 transfers methanol in substantially liquid form into the reactive distillation column 150 through conduits 147 and 149.

Solid acidic catalyst is present in the reactive distillation column 150 to allow solutions containing water, methanol, formaldehyde, methylal and one or more other polyoxymethylene dimethyl ethers to be brought into solid-liquid contact counter-currently with the catalyst to form products including methylal and higher molecular weight polyoxymethylene dimethyl ethers. More volatile reaction products are taken overhead from the high efficiency separation apparatus, whereas water and less volatile reaction products are carried down the high efficiency separation apparatus.

The overhead vapor stream from reactive distillation column 150 is transferred through conduit 152 into condenser 154. A suitable portion of condensate from condenser 154 is refluxed into reactive distillation column 150 through conduits 155 and 156. A product stream containing methylal is transferred through conduit 158 to product storage (not shown). Conduit 159 supplies pump 160 with liquid containing higher molecular weight polyoxymethylene dimethyl ethers from the bottom of column 150. A suitable portion of liquid from the bottom of column 150 is transferred, by means of pump 160, through conduits 162 and 163 into reboiler 164 which is in flow communication with the bottom of the column by means of conduit 166. A product stream containing higher molecular weight polyoxymethylene dimethyl ethers is transferred through conduit 168 to product storage (not shown). Preferably, an anion exchange resin is disposed within a section of the distillation column below the stages of contact with the acidic catalyst to form an essentially acid-free mixture.

An aqueous side stream containing low levels of unreacted formaldehyde and/or methanol is discharged from column 150 through conduit 172. The side stream from column 150 is transferred to waste disposal (not shown).

In this embodiment of the invention, tungsten oxide catalyzes the conversion of dimethyl ether to formaldehyde by an oxidation reaction at temperatures in a range from about 350° to about 600° C., preferably in a range from about 400° to about 500° C.:

$$CH_3OCH_3 + O_2 \rightarrow 2CH_2O + H_2O$$

In this case, a large excess of air is necessary to obtain maximum yields and to avoid explosive feed concentrations. Some flexibility exists in the explosive limits, depending upon the temperature, pressure, and normal moisture content of the air. However, normal practical limitations appear to set a lower boundary between 8 mol percent and 10 mol percent in the reactor feed.

Several side reactions occur, especially those producing carbon monoxide, formic acid, and dimethyl ether. However, because of a lower reaction temperature, the extent of these reactions is smaller than in the silver-catalyzed process.

In view of the features and advantages of the continuous catalytic processes for direct condensation of formaldehyde and dimethyl ether to form a mixture containing one or more polyoxymethylene dimethyl ethers in accordance with this invention, as compared to the known methanol condensation systems previously used, the following examples are given.

EXAMPLES 1 to 3

In Examples 1, 2 and 3 a crystalline borosilicate catalyst exhibiting the MFI crystal structure was used to convert a predominately dimethyl ether feedstream and a liquid feedstream of aqueous formaldehyde in methanol. Effluent of the condensation reactor comprised water, methanol, formaldehyde, dimethyl ether, methylal and higher polyoxymethylene dimethyl ethers having a structure represented by the type formula $$CH_3O(CH_2O)_nCH_3$$

in which formula n is a number from 1 to about 7.

Crystalline borosilicate molecular sieve in the form of an extrudate (1/16 inch) was calcined overnight at 500° C. The calcined extrudate was crushed and sieved to 18–40 mesh. A tubular quartz reactor was charged with 3.27 grams (5 cc) of the sieved particles. The tubular quartz reactor (approx. 10 mm inside diameter) was equipped with a quartz thermowell terminating at about the midpoint of the catalyst bed.

A liquid feed solution was prepared in a pressurized 50 mL autoclave using 11.13 grams of paraformaldehyde (95%), 15.94 grams of methanol, and 1.80 grams of water. Contents of the autoclave were stirred and heated to temperatures of 130° to 140° C. for 1 hour, and then cooled. The resulting solution was fed by a syringe pump into a preheat zone above the catalyst bed. Using mass flow controllers, a gas feed mixture of dimethyl ether and nitrogen was also fed to the top of the reactor.

Liquid products from the reactor were collected in a cool (0° C.) 25 mL flask for subsequent weighing and GC analysis. Gases exiting the collection flask were analyzed by on-line GC using both TCD and FID detectors. Samples of liquid products were collected during sampling intervals of 2 hours over an approximately 16 hour period of operation. Gas analyses were obtained by GC during each sampling interval.

Two samples were collected while temperature of the catalyst bed was controlled to three progressively higher temperatures. Each sample was about 7 grams. Operating conditions and results are summarized in Tables I–III.

Net conversion of the methoxy moiety (Net MeO, percent) is an indication of the conversion of groups regardless of origin, i.e., both methanol (MeOH) which has one MeO per mole and dimethyl ether (DME) which has two MeO per mol. Net MeO may be expressed as follows:

$$\text{Net MeO} = 100 \times \frac{(\text{MeOH} + 2\,\text{DME})_{feed} - (\text{MeOH} + 2\,\text{DME})_{effluent}}{(\text{MeOH} + 2\,\text{DME})_{feed}}$$

EXAMPLE 4

In this example an acidic catalyst was used to convert a liquid feedstream of formaldehyde in methanol under conditions which allowed gas-liquid contacting of the solid catalyst (trickle bed operation). Effluent of the condensation comprised water, methanol, formaldehyde, dimethyl ether, methylal and higher polyoxymethylene dimethyl ethers.

The acidic catalyst was a proton exchanged sulfonic acid based ion exchange resin. This polymeric material is a Bronstead (protic) acid. A tubular quartz reactor was charged with 5 cc of acidic catalyst particles. The tubular quartz reactor (approx. 10 mm inside diameter) was equipped with a quartz thermowell terminating at about the midpoint of the catalyst bed.

A liquid feed solution was prepared in a pressurized 50 mL autoclave using 7.42 grams of paraformaldehyde (95%) and 15.93 grams of methanol. Contents of the autoclave were stirred and heated to temperatures of 130° to 140° C. for 1 hour, and then cooled. The resulting solution was fed by a syringe pump into a preheat zone above the catalyst bed. Using mass flow controllers, a gas feed mixture of dimethyl ether and nitrogen was also fed to the top of the reactor.

Liquid products from the reactor were collected in a cool (0° C.) 25 mL flask for subsequent weighing and GC analysis. Gases exiting the collection flask were analyzed by on-line GC using both TCD and FID detectors. Operating conditions and results are summarized in Table IV.

EXAMPLE 5

In this example an acidic catalyst was used to convert a mixture of formaldehyde in methanol under conditions which allowed liquid contacting of the solid catalyst. A liquid feed solution was prepared in a pressurized 50 mL autoclave using 7.4 grams of paraformaldehyde (95%) and 15.9 grams of methanol. Contents of the autoclave were stirred and heated to temperatures of 130° to 140° C. for 1 hour, and then cooled. The autoclave was opened and charged with 1.0 gram of catalyst. Contents of the autoclave were heated to reaction temperature for 2 to 3 hours with stirring. After cooling to ambient temperature and settling, the supernatant liquid was sampled for GC analysis and formaldehyde titration analysis. Results are summarized in Table V.

EXAMPLE 6

Products of several condensation runs were composited, and the composite vacuum filtered through a medium glass frit. A 90 gram aliquot of filtrate was shaken with 20 grams of basic ion-exchange resin beads (DOWEX 66) which were then allowed to settle for one hour. The resulting supernatant liquid was then gravity filtered through a medium paper filter. A suitable amount (54 grams) of molecular sieve type 3A, which had been activated by calcination at about 538° C., was mixed into the filtrate, and the mixture allowed to stand overnight at ambient temperatures. Liquid was separated from the sieve by vacuum filtration through a medium glass frit. A 45.97 gram aliquot of this acid-free, dry filtrate was charged to a small distillation apparatus consisting of a 100 mL 3-neck flask, a fractionating column and condenser. The charge was distilled into eight overhead fractions which were collected at temperature cuts according to the following schedule.

Schedule of Overhead and Bottom Temperatures

| Fraction Number | Temperatures, ° C. | |
|---|---|---|
| | Overhead | Bottom |
| 1 | 42 to 46 | 70 to 94 |
| 2 | 47 to 76 | 95 to 109 |
| 3 | 77 to 94 | 110 to 118 |
| 4 | 95 to 100 | 119 to 127 |
| 5 | 101 to 107 | 128 to 136 |
| 6 | 108 to 112 | 137 to 146 |
| 7 | 113 to 123 | 147 to 162 |
| 8 | 124 to 150 | 163 to 174 |

White solids (possibly paraformaldehyde) were observed in the column and condenser during cuts 2 through 4, but not thereafter. Composition of the distilled fraction and bottoms are given in Table IV.

For the purposes of the present invention, "predominantly" is defined as more than about fifty percent. "Substantially" is defined as occurring with sufficient frequency or being present in such proportions as to measurably affect macroscopic properties of an associated compound or system. Where the frequency or proportion for such impact is not clear, substantially is to be regarded as about twenty per cent or more. The term "essentially" is defined as absolutely except that small variations which have no more than a negligible effect on macroscopic qualities and final outcome are permitted, typically up to about one percent.

TABLE I

Conversion of Feedstreams at about 100° C.
Using a Crystalline Borosilicate Catalyst Exhibiting the MFI Crystal Structure

| Temperature, ° C. | 100 | 101 |
|---|---|---|
| Run Time, min | 95 | 155 |
| Gas Feed, mol percent | | |
| Nitrogen | 32.925 | 32.925 |
| DME | 67.075 | 67.075 |
| Liquid Feed, weight percent | | |
| Methanol | 55.20 | 55.20 |
| Formaldehyde | 38.55 | 38.55 |
| Water | 6.25 | 6.25 |
| Feed Rates | | |
| Gas scc/min | 34.1 | 34.1 |
| Liquid mL/min | 0.00756 | 0.00756 |
| Conversions, mole percent | | |
| Methanol | 67.15 | 66.96 |
| DME | 4.36 | 2.71 |
| Net MeO | 28.20 | 27.10 |
| Formaldehyde | 78.84 | 78.84 |
| Selectivities, percent | | |
| Gases | | |
| CO | 0 | 0 |
| $CO_2$ | 0 | 0 |
| Liquids | | |
| Methylal | 80.548 | 78.269 |
| HPE | 0.750 | 0.751 |

TABLE I-continued

Conversion of Feedstreams at about 100° C.
Using a Crystalline Borosilicate Catalyst Exhibiting the MFI
Crystal Structure

| | | |
|---|---|---|
| DME/MeOH | 5.38 | 5.44 |
| Carbon Balance | 92.57 | 93.39 |

Where MeOH is methanol, HPE is higher polyoxymethylene dimethyl ethers which are $CH_3O(CH_2O)_nCH_3$ having n greater than 1, MeO is methoxy moiety, and DME is dimethyl ether.

TABLE II

Conversion of Feedstreams at about 130° C.
Using a Crystalline Borosilicate Catalyst Exhibiting the MFI
Crystal Structure

| | | |
|---|---|---|
| Temperature, ° C. | 132 | 131 |
| Run Time, min | 245 | 305 |
| Gas Feed, mol percent | | |
| Nitrogen | 32.925 | 32.925 |
| DME | 67.075 | 67.075 |
| Liquid Feed, weight percent | | |
| Methanol | 55.20 | 55.20 |
| Formaldehyde | 38.55 | 38.55 |
| Water | 6.25 | 6.25 |
| Feed Rates | | |
| Gas scc/min | 34.1 | 34.1 |
| Liquid mL/min | 0.00756 | 0.00756 |
| Conversions, mole percent | | |
| Methanol | 53.59 | 53.68 |
| DME | 5.12 | 4.75 |
| Net MeO | 23.52 | 23.33 |
| Formaldehyde | 86.71 | 86.71 |
| Selectivities, percent | | |
| Gases | | |
| CO | 0 | 0 |
| $CO_2$ | 0.095 | 0.086 |
| Liquids | | |
| Methylal | 64.480 | 64.699 |
| HPE | 0.323 | 0.326 |
| DME/MeOH | 3.48 | 3.50 |
| Carbon Balance | 91.63 | 91.53 |

Where MeOH is methanol, HPE is higher polyoxymethylene dimethyl ethers which are $CH_3O(CH_2O)_nCH_3$ having n greater than 1, MeO is methoxy moiety, and DME is dimethyl ether.

TABLE III

Conversion of Feedstreams at about 160° C.
Using a Crystalline Borosilicate Catalyst Exhibiting the MFI
Crystal Structure

| | | |
|---|---|---|
| Temperature, ° C. | 164 | 160 |
| Run Time, min | 345 | 400 |
| Gas Feed, mol percent | | |
| Nitrogen | 32.925 | 32.925 |
| DME | 67.075 | 67.075 |
| Liquid Feed, weight percent | | |
| Methanol | 55.20 | 55.20 |
| Formaldehyde | 38.55 | 38.55 |
| Water | 6.25 | 6.25 |
| Feed Rates | | |
| Gas scc/min | 34.1 | 34.1 |
| Liquid mL/min | 0.00756 | 0.00756 |

TABLE III-continued

Conversion of Feedstreams at about 160° C.
Using a Crystalline Borosilicate Catalyst Exhibiting the MFI
Crystal Structure

| | | |
|---|---|---|
| Conversions, mole percent | | |
| Methanol | 34.82 | 35.19 |
| DME | 7.45 | 1.12 |
| Net MeO | 17.84 | 14.05 |
| Formaldehyde | 90.59 | 90.59 |
| Selectivities, percent | | |
| Gases | | |
| CO | 0 | 0 |
| $CO_2$ | 0.370 | 0.317 |
| Liquids | | |
| Methylal | 42.970 | 43.410 |
| HPE | 0.094 | 0.096 |
| DME/MeOH | 2.37 | 2.54 |
| Carbon Balance | 92.40 | 94.76 |

Where MeOH is methanol, HPE is higher polyoxymethylene dimethyl ethers which are $CH_3O(CH_2O)_nCH_3$ having n greater than 1, MeO is methoxy moiety, and DME is dimethyl ether.

TABLE IV

Trickle Bed Conversion of Feedstreams Using an Ion Exchange
Resin Based Catalyst Exhibiting Bronstead Acid Sites

| | |
|---|---|
| Temperature, ° C. | 71 |
| Feed Rates | |
| Gas scc/min | 10 |
| Liquid mL/min | 0.0756 |
| Conversions, mole percent | |
| Methanol | 87.04 |
| Formaldehyde | 92.27 |
| Selectivities, percent | |
| Methylal | 97.78 |
| HPE | 1.77 |

Where HPE is higher polyoxymethylene dimethyl ethers which are $CH_3O(CH_2O)_nCH_3$ having n greater than 1.

TABLE V

Liquid Phase Conversion Using an Ion Exchange Resin Based
Catalyst Exhibiting Bronstead Acid Sites

| | |
|---|---|
| Temperature, ° C. | 67 |
| Conversions, mole percent | |
| Methanol | 73.38 |
| Formaldehyde | 77.91 |
| Selectivities, percent | |
| Methylal | 88.20 |
| HPE | 6.03 |

Where HPE is higher polyoxymethylene dimethyl ethers which are $CH_3O(CH_2O)_nCH_3$ having n greater than 1.

TABLE VI

COMPOSITION OF OVERHEAD FRACTIONS AND BOTTOMS

| | Compound | | | | $CH_3O(CH_2O)_nCH_3$ where the value of n is: | | | | | |
|---|---|---|---|---|---|---|---|---|---|---|
| Fraction | Methylal | Methanol | Hemiacetals | Trioxane | 2 | 3 | 4 | 5 | 6 | 7 |
| Starting | 49.95 | 0.0 | 0.69 | 2.42 | 22.60 | 12.42 | 6.40 | 3.15 | 1.45 | 0.61 |
| 1 | 97.21 | 0.95 | 0.05 | 0.0 | 0.46 | 0 | 0 | 0 | 0 | 0 |
| 2 | 93.83 | 2.52 | 0.38 | 0.0 | 2.84 | 0 | 0 | 0 | 0 | 0 |
| 3 | 20.81 | 12.92 | 8.85 | 2.39 | 54.80 | 0.17 | 0 | 0 | 0 | 0 |
| 4 | 3.24 | 11.12 | 6.40 | 4.49 | 74.19 | 0.57 | 0 | 0 | 0 | 0 |
| 5 | 0.56 | 8.47 | 2.29 | 5.83 | 82.07 | 0.78 | 0 | 0 | 0 | 0 |
| 6 | 0.40 | 3.10 | 0.16 | 7.21 | 88.05 | 1.08 | 0 | 0 | 0 | 0 |
| 7 | 0.43 | 0.99 | 0.0 | 9.38 | 86.60 | 2.55 | 0.05 | 0 | 0 | 0 |
| 8 | 0.32 | 0.47 | 0.0 | 11.77 | 82.98 | 4.37 | 0.08 | 0 | 0 | 0 |
| Bottoms | 0.29 | 0.02 | 0.0 | 0.54 | 1.10 | 49.49 | 26.19 | 13.05 | 6.34 | 2.96 |

That which is claimed is:

1. A process for dehydrogenation of dimethyl ether to form a source of formaldehyde comprising continuously contacting a gaseous feedstream comprising dimethyl ether, dioxygen and diluent with a catalytically effective amount of an oxidation promoting catalyst comprising tungsten oxide as an essential catalyst component at elevated temperatures in a range from about 350° to about 600° C. to form a gaseous mixture comprising formaldehyde, dimethyl ether, dioxygen, diluent, carbon monoxide, carbon dioxide and water vapor; cooling the gaseous dehydrogenation mixture with a liquid by using at least one continuous adsorption column with cooling to temperatures in a range downward from about 100° C. to 15° C. and separating the resulting liquid source of formaldehyde which contains about 30 to about 85 percent by weight formaldehyde in methanol solution containing less than 5 percent water from a mixture of gases comprising dioxygen, diluent, carbon monoxide, carbon dioxide and water vapor; and recycling at least a portion of the mixture to the continuously contact gaseous feedstream with the oxidation promoting catalyst.

2. The process according to claim 1 wherein the oxidation promoting catalyst consists of a composition comprising $\beta\text{-Mo}_{(1-x)}W_x O_3$, where x is a number between 0 and 1, and wherein the elevated temperatures are in a range from about 200° to about 450° C.

3. A process for the catalytic production of a mixture of oxygenated organic compounds suitable as a blending component of fuel for use in compression ignition internal combustion engines, which process comprises providing a feedstream comprising methanol, a soluble condensation promoting component capable of activating a heterogeneous acidic catalyst and a source of formaldehyde formed by the conversion of dimethyl ether in the presence of a catalyst comprising tungsten oxide as an essential catalyst component; heating the feedstream with the heterogeneous acidic catalyst under conditions of reaction sufficient to form an effluent of condensation comprising water, methanol and one or more polyoxymethylene dimethyl ethers having a structure represented by the formula $$CH_3O(CH_2O)_nCH_3$$

where n is a number from 1 to about 10; contacting the effluent of condensation with an anion exchange resin to form an essentially acid-free mixture; and distilling the mixture to separate methylal from higher polyoxymethylene dimethyl ethers; wherein the soluble condensation promoting component capable of activating the heterogeneous acidic catalyst comprises at least one member of the group consisting of low boiling, monobasic organic acids.

4. The process according to claim 3 wherein the acidic catalyst comprises a sulfonated tetrafluoroethylene resin derivative.

5. The process according to claim 3 wherein the heating of the feedstream with the acidic catalyst is carried out at temperatures in a range from about 45° to about 90° C. and employs at least one catalytic distillation column having internal and/or external stages of contact with the acidic catalyst and internal zones to separate methylal from higher polyoxymethylene dimethyl ethers.

6. The process according to claim 5 wherein at least a liquid portion of the effluent containing polyoxymethylene dimethyl ethers is contacted with an anion exchange resin disposed within a section of the distillation column below the stages of contact with the acidic catalyst to form an essentially acid-free mixture.

7. The process according to claim 6 wherein the essentially acid-free mixture of polyoxymethylene dimethyl ethers is fractionated within a section of the distillation column below the stages of contact with the acidic catalyst to provide an aqueous side-stream which is withdrawn from the distillation column, and an essentially water-free mixture of polyoxymethylene dimethyl ethers having values of n greater than 1 which mixture is withdrawn from the distillation column near its bottom.

8. The process according to claim 5 wherein a source of methanol is admixed with the feedstream, and/or into the stages of contact with the acidic catalyst.

9. The process according to claim 1 which further comprises formation of the feedstream by a process comprising continuously contacting a gaseous feedstream comprising dimethyl ether, dioxygen and diluent with a catalytically effective amount of an oxidation promoting catalyst comprising tungsten oxide as an essential catalyst component at elevated temperatures to form a gaseous mixture comprising formaldehyde, dimethyl ether, dioxygen, diluent, carbon monoxide, carbon dioxide and water vapor; cooling the gaseous oxidation mixture with a liquid to take up and hold formaldehyde therein; and separating the resulting liquid source of formaldehyde from a mixture of gases comprising dioxygen, diluent, carbon monoxide, carbon dioxide and water vapor.

10. The process according to claim 9 wherein at least a portion of the mixture of gases separated from the resulting liquid source of formaldehyde is recycled into the gaseous feedstream.

11. The process according to claim 9 wherein the source of dioxygen in the gaseous feedstream is a dioxygen enriched gas stream obtained by physically separating a gaseous mixture, containing at least about 10 volume percent dioxygen, into a dioxygen depleted stream and a dioxygen-enriched gas stream.

12. A process for the catalytic production of a mixture of oxygenated organic compounds suitable as a blending component of fuel for use in compression ignition internal combustion engines, which process comprises providing a source of formaldehyde formed by the conversion of dimethyl ether in the presence of a catalyst comprising tungsten oxide; and contacting the source of formaldehyde and a predominately dimethyl ether feedstream with a condensation promoting catalyst capable of hydrating dimethyl ether, in a form which is heterogeneous to the feedstream, under conditions of reaction sufficient to form an effluent of condensation comprising water, methanol, formaldehyde, dimethyl ether, one or more polyoxymethylene dimethyl ethers having a structure represented by the formula $$CH_3O(CH_2O)_nCH_3$$

where n is a number from 1 to about 10.

13. The process according to claim 1 wherein the conditions of reaction including temperatures in a range from about 50° to 130° C., and the condensation promoting catalyst capable of hydrating dimethyl ether comprises at least one member of the group consisting crystalline metallosilicates which exhibit the MFI crystal structure and have a silicon-to-aluminum atomic ratio of at least 10, and crystalline borosilicates which have the following compositions in terms of mole ratios of oxides:

$$0.9\pm0.2M_{2/n}O:B_2O_3:Y\ SiO_2:Z\ H_2O,$$

wherein M is at least one cation having a valence of n, Y is between 4 and about 600, and Z is between 0 and about 160 and exhibit the MFI crystal structure.

14. The process according to claim 13 which further comprises fractionating the effluent of condensation to obtain an overhead stream, which is predominantly dimethyl ether, and an essentially dimethyl ether-free bottom stream comprising formaldehyde, methanol and at least methylal, and heating the bottom stream with an acidic catalyst, which is heterogeneous to the feedstream, under conditions of reaction sufficient to convert formaldehyde and methanol present to methylal and higher polyoxymethylene dimethyl ethers.

15. The process according to claim 14 wherein the heating of the bottom stream with the acidic catalyst employs at least one catalytic distillation column with internal and/or external stages of contact with the acidic catalyst, and internal zones to separate the methylal from the higher polyoxymethylene dimethyl ethers.

16. The process according to claim 15 wherein the mixture of polyoxymethylene dimethyl ethers is contacted with an anion exchange resin disposed within a section of the distillation column below the stages of contact with the acidic catalyst to form an essentially acid-free mixture.

17. The process according to claim 16 wherein the essentially acid-free mixture of polyoxymethylene dimethyl ethers is fractionated within a section of the distillation column below the stages of contact with the acidic catalyst to provide an aqueous side-stream which is withdrawn from the distillation column, and an essentially water-free mixture of polyoxymethylene dimethyl ethers having values of n greater than 1 which mixture is withdrawn from the distillation column near its bottom.

18. The process according to claim 17 wherein at least a portion of the aqueous side-stream is used for recovery of an aqueous formaldehyde solution in an adsorption column.

19. The process according to claim 14 wherein the at least a portion of the overhead stream containing dimethyl ether is recycled to the contacting with the condensation-promoting catalyst of claim 1.

20. The process according to claim 13 wherein the source of formaldehyde is formed by a process comprising continuously contacting a gaseous feedstream comprising dimethyl ether, dioxygen and diluent with a catalytically effective amount of an oxidation promoting catalyst comprising tungsten oxide as an essential catalyst component at elevated temperatures to form a gaseous mixture comprising formaldehyde, dimethyl ether, dioxygen, diluent, carbon monoxide, carbon dioxide and water vapor; cooling the gaseous oxidation mixture with an adsorption liquid and adsorbing formaldehyde therein; and separating the resulting liquid source of formaldehyde from a mixture of gases comprising dioxygen, diluent, carbon monoxide, carbon dioxide and water vapor.

\* \* \* \* \*

UNITED STATES PATENT AND TRADEMARK OFFICE
CERTIFICATE OF CORRECTION

PATENT NO. : 6,392,102 B1
DATED : May 21, 2002
INVENTOR(S) : Gary P. Hagen and Michael J. Spangler It is certified that error appears in the above-identified patent and that said Letters Patent is hereby corrected as shown below:

Column 4,
Line 43, "(Rosinsid, et al., in U.S." should read -- (Rosinski, et al., in U.S. --

Column 5,
Line 44, "fuel,, when blended with" should read -- fuel, when blended with --

Column 12,
Line 55, "Amberlite 200ºC. of Organic" should read -- Amberlite 200C of Organic --

Column 14,
Line 39, "$Mo_{0.95}W_{x0.5}O_3$," should read -- $Mo_{0.95}W_{x0.05}O_3$, --

Column 25,
Line 38, "the continuously contact gaseous" should read -- the continuously contacted gaseous--

Signed and Sealed this

Twenty-third Day of July, 2002

Attest:

JAMES E. ROGAN
Attesting Officer
Director of the United States Patent and Trademark Office